(12) United States Patent
Lin et al.

(10) Patent No.: US 9,282,924 B2
(45) Date of Patent: Mar. 15, 2016

(54) MEDICAL SENSOR WITH TEMPERATURE CONTROL

(75) Inventors: Andy S. Lin, Boulder, CO (US); Youzhi Li, Longmont, CO (US); Bo Chen, Louisville, CO (US); Daniel Lisogurski, Boulder, CO (US); Friso Schlottau, Lyons, CO (US)

(73) Assignee: Covidien LP, Mansfield, MA (US)

( * ) Notice: Subject to any disclaimer, the term of this patent is extended or adjusted under 35 U.S.C. 154(b) by 697 days.

(21) Appl. No.: 13/077,164

(22) Filed: Mar. 31, 2011

(65) Prior Publication Data

US 2012/0248985 A1    Oct. 4, 2012

(51) Int. Cl.
*A61B 5/1455* (2006.01)
*A61B 5/00* (2006.01)

(52) U.S. Cl.
CPC ........... *A61B 5/14551* (2013.01); *A61B 5/6826* (2013.01); *A61B 2560/0252* (2013.01); *A61B 2560/0266* (2013.01)

(58) Field of Classification Search
CPC ........... A61B 5/14532; A61B 5/14551; A61B 5/1495; A61B 5/1455; A61B 5/0095; A61B 5/1459; A61B 8/4281; A61B 5/0059; A61B 2562/146; A61B 1/0638; A61B 2560/0223; G01N 21/359; G01N 2021/3144; G01N 2201/1211
USPC ......... 315/149, 152, 153, 246, 287, 291, 299, 315/307–309; 600/310, 331, 333, 336
See application file for complete search history.

(56) References Cited

U.S. PATENT DOCUMENTS

| 4,913,150 A | 4/1990 | Cheung et al. |
| 4,926,867 A | 5/1990 | Kanda et al. |
| 5,007,423 A * | 4/1991 | Branstetter et al. .. A61B 5/1491 600/334 |
| 5,066,859 A | 11/1991 | Karkar et al. |
| 5,259,381 A | 11/1993 | Cheung et al. |
| 5,361,758 A | 11/1994 | Hall et al. |
| 5,427,093 A | 6/1995 | Ogawa et al. |
| 5,477,853 A | 12/1995 | Farkas et al. |

(Continued)

FOREIGN PATENT DOCUMENTS

| DE | 69123448 | 5/1997 |
| WO | 9316629 A1 | 9/1993 |
| WO | 2006109072 A2 | 10/2006 |

OTHER PUBLICATIONS

Buschman, J.P., et al.; "Principles and Problems of Calibration of Fetal Oximeters," Biomedizinische Technik, vol. 42, pp. 265-266 (1997).

(Continued)

*Primary Examiner* — Alexandedr H Taningco
*Assistant Examiner* — Christopher Lo
(74) *Attorney, Agent, or Firm* — Fletcher Yoder PC (57) ABSTRACT

Embodiments of the present disclosure relate to techniques for controlling the temperature of light sources within physiological sensors in order to regulate the wavelengths emitted by the light sources. The sensors may include a temperature control element that is designed to provide heating and/or cooling to the light sources. The sensors also may include a temperature sensor designed to detect the temperature of the light sources. Based on the detected temperature, a controller can vary the amount of heating and/or cooling provided by the temperature control element to maintain the temperature of the light sources at a desired temperature or within a desired temperature range.

20 Claims, 6 Drawing Sheets

(56) References Cited

U.S. PATENT DOCUMENTS

| | | |
|---|---|---|
| 5,673,692 A | 10/1997 | Schulze et al. |
| 6,356,774 B1 | 3/2002 | Bernstein et al. |
| 6,400,971 B1 | 6/2002 | Finarov et al. |
| 6,512,937 B2 | 1/2003 | Blank et al. |
| 6,556,852 B1 | 4/2003 | Schulze et al. |
| 6,850,789 B2 | 2/2005 | Schweitzer, Jr. et al. |
| 6,902,291 B2 | 6/2005 | Rizkin et al. |
| 7,496,391 B2 | 2/2009 | Diab et al. |
| 7,525,191 B2 | 4/2009 | Nakazato et al. |
| 7,586,125 B2 | 9/2009 | Dai et al. |
| 7,731,377 B2 | 6/2010 | Moriya et al. |
| 7,761,127 B2 | 7/2010 | Al-Ali et al. |
| 2003/0109776 A1* | 6/2003 | Jacques ............... A61B 5/1495 600/331 |
| 2005/0283081 A1 | 12/2005 | Lin et al. |
| 2007/0043278 A1* | 2/2007 | Mannheimer et al. ............... A61B 5/14551 600/323 |
| 2007/0197887 A1 | 8/2007 | Lunak et al. |
| 2008/0242958 A1* | 10/2008 | Al-Ali et al. ....... A61B 5/02427 600/323 |
| 2010/0022859 A1* | 1/2010 | Al-Ali et al. ....... A61B 5/14552 600/310 |
| 2010/0096993 A1* | 4/2010 | Ashdown et al. ..... F21V 29/004 315/113 |
| 2011/0190600 A1* | 8/2011 | McKenna et al. ......... A61B 5/01 600/301 |
| 2012/0071739 A1 | 3/2012 | Chen et al. |

OTHER PUBLICATIONS

Lopez-Silva, S.M., et al.; "Transmittance Photoplethysmography and Pulse Oximetry With Near Infrared Laser Diodes," IMTC 2004—Instrumentation and Measurement Technology Conference, Como, Italy, May 18-20, 2004; pp. 718-723.

U.S. Appl. No. 12/751,806, filed Mar. 31, 2010, Mckenna et al.

* cited by examiner

MEDICAL SENSOR WITH TEMPERATURE CONTROL

BACKGROUND

The present disclosure relates generally to medical devices and, more particularly, to sensors used for sensing physiological parameters of a patient.

This section is intended to introduce the reader to various aspects of art that may be related to various aspects of the present disclosure, which are described and/or claimed below. This discussion is believed to be helpful in providing the reader with background information to facilitate a better understanding of the various aspects of the present disclosure. Accordingly, it should be understood that these statements are to be read in this light, and not as admissions of prior art.

In the field of medicine, doctors often desire to monitor certain physiological characteristics of their patients. To allow such monitoring, various types of sensors and monitors may be employed by caregivers. For example, to measure certain characteristics, optical based sensors may be utilized that transmit electromagnetic radiation, such as light, through a patient's tissue and then photoelectrically detect the absorption and scattering of the transmitted or reflected light in such tissue. The physiological characteristics of interest may then be calculated based upon the amount of light absorbed and/or scattered or based upon changes in the amount of light absorbed and/or scattered. In such measurement approaches, the light passed through the tissue is typically selected to be of one or more wavelengths that may be absorbed and/or scattered by one or more constituents of the blood or tissue in an amount correlative to the amount of the constituents present in the blood or tissue.

One technique for monitoring certain physiological characteristics of a patient is commonly referred to as pulse oximetry, and the devices built based upon pulse oximetry techniques are commonly referred to as pulse oximeters. Pulse oximetry may be used to measure various blood flow characteristics, such as the blood-oxygen saturation of hemoglobin ($SpO_2$) in arterial blood, the volume of individual blood pulsations supplying the tissue, and/or the rate of blood pulsations corresponding to each heartbeat of a patient. In fact, the "pulse" in pulse oximetry refers to the time varying amount of arterial blood in the tissue during each cardiac cycle.

Pulse oximeters typically utilize a non-invasive sensor that transmits light through a patient's tissue and that photoelectrically detects the absorption and/or scattering of the transmitted light in such tissue. One or more of the above physiological characteristics may then be calculated based upon the amount of light absorbed or scattered. As noted above, the light passed through the tissue is typically selected to be of one or more wavelengths that may be absorbed or scattered by the blood in an amount con'elative to the amount of the blood constituent present in the blood. The amount of light absorbed and/or scattered may then be used to estimate the amount of blood constituent in the tissue using various algorithms.

The light sources used in pulse oximeters, as well as other medical devices, may be designed to emit wavelengths that correspond to the physiological characteristics to be determined. For example, pulse oximeters may utilize light sources that emit in at least two spectral regions, one that emits in the red region (typically about 660 nm) and one in the near infrared region (typically about 900 nm). The absorbance ratios for these wavelengths can then be used to determine the oxygenation of a patient's blood. In another example, some pulse oximeters may replace the 660 nm emitter with an emitter designed to emit light in the far red region (typically about 730 nm), The 730 nm emitter may then be used in conjunction a 900 nm emitter to determine the oxygenation of a patient's blood. The use of a 730 nm emitter and a 900 nm emitter may provide greater accuracy when $SpO_2$ is low (e.g., in the range below 75%).

The wavelengths emitted by the sensors can vary between sensors and can vary during operation of the medical device. For example, due to manufacturing variations, light sources, such as light emitting diodes (LEDs) or laser diodes, may emit slightly different wavelengths. Accordingly, calibration models may be included in pulse oximeters to account for these variations. However, the inclusion of calibration models can complicate manufacturing and introduce additional costs. In another example, changes in temperature can affect the wavelength emitted by the sensors. For example, the ambient temperature may vary and/or the temperature of the sensor itself may vary as the driving strength changes. These variations in a sensor's emitted wavelength may affect the accuracy of the determined physical characteristics.

BRIEF DESCRIPTION OF THE DRAWINGS

Advantages of the disclosed techniques may become apparent upon reading the following detailed description and upon reference to the drawings in which.

DETAILED DESCRIPTION OF SPECIFIC EMBODIMENTS

One or more specific embodiments of the present techniques will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

The present disclosure relates to techniques for controlling the temperature of light sources within physiological sensors. The sensors may include a temperature control element designed to provide heating and/or cooling to the light sources. The light sources, in certain embodiments, may be light emitting diodes or laser diodes. The sensors also may include a temperature sensor designed to detect the temperature of the light sources. Based on the detected temperature, a controller can vary the amount of heating and/or cooling provided by the temperature control element to maintain the temperature of the light sources at a desired temperature or within a desired temperature range. In another embodiment, the detector may be sensitive to the wavelength of received light and may estimate temperature or temperature changes based on absolute wavelength, the absolute wavelength relative to a calibration, from a previously measured wavelength, or based on wavelength changes and a calibration. In these embodiments, the controller may vary the amount of heating and/or cooling provided by the temperature control element to compensate for the temperature change determined based on information from the detector.

The wavelengths of light emitted by the light sources can vary with temperature. Accordingly, in certain embodiments, the controller can be employed to maintain the temperature of the light sources at a temperature that enables the light sources to produce desired wavelengths of light. For example, the temperature control element may be employed to adjust the wavelength emitted the light sources to correspond to a calibration wavelength. In another example, the temperature control element may be employed to allow one light source to be employed to produce multiple wavelengths of light used to determine certain physiological parameters, such as total hemoglobin. Further, the temperature control element can be employed to provide temperature adjustments that compensate for changes in the ambient temperature and/or the operational temperature of the sensor. In these embodiments, the temperature control element may be employed to maintain a consistent temperature for the emitters, which can provide repeatability in the measurements taken using the emitters. Moreover, the temperature control element can be employed to warm the tissue beneath the sensor to promote increased blood flow and/or to cool the sensor, for example, to maintain the tissue beneath the sensor at a comfortable temperature.

According to certain embodiments, the temperature control element may include a thermoelectric element that is switchable between a cooling mode and a heating mode. The controller may vary the level of power provided to the thermoelectric element to adjust the amount of heating or cooling provided by the thermoelectric element. Further, the controller may govern one or more switches that can reverse the direction of current flow through the thermoelectric element to switch the thermoelectric element between the heating mode and the cooling mode. In other embodiments, the temperature control element may include a heating element, such as a resistive heater, that provides heating, while a thermoelectric cooler provides cooling. Moreover, in yet other embodiments, the temperature control element may be designed to provide only heating or only cooling.

Figure 1:
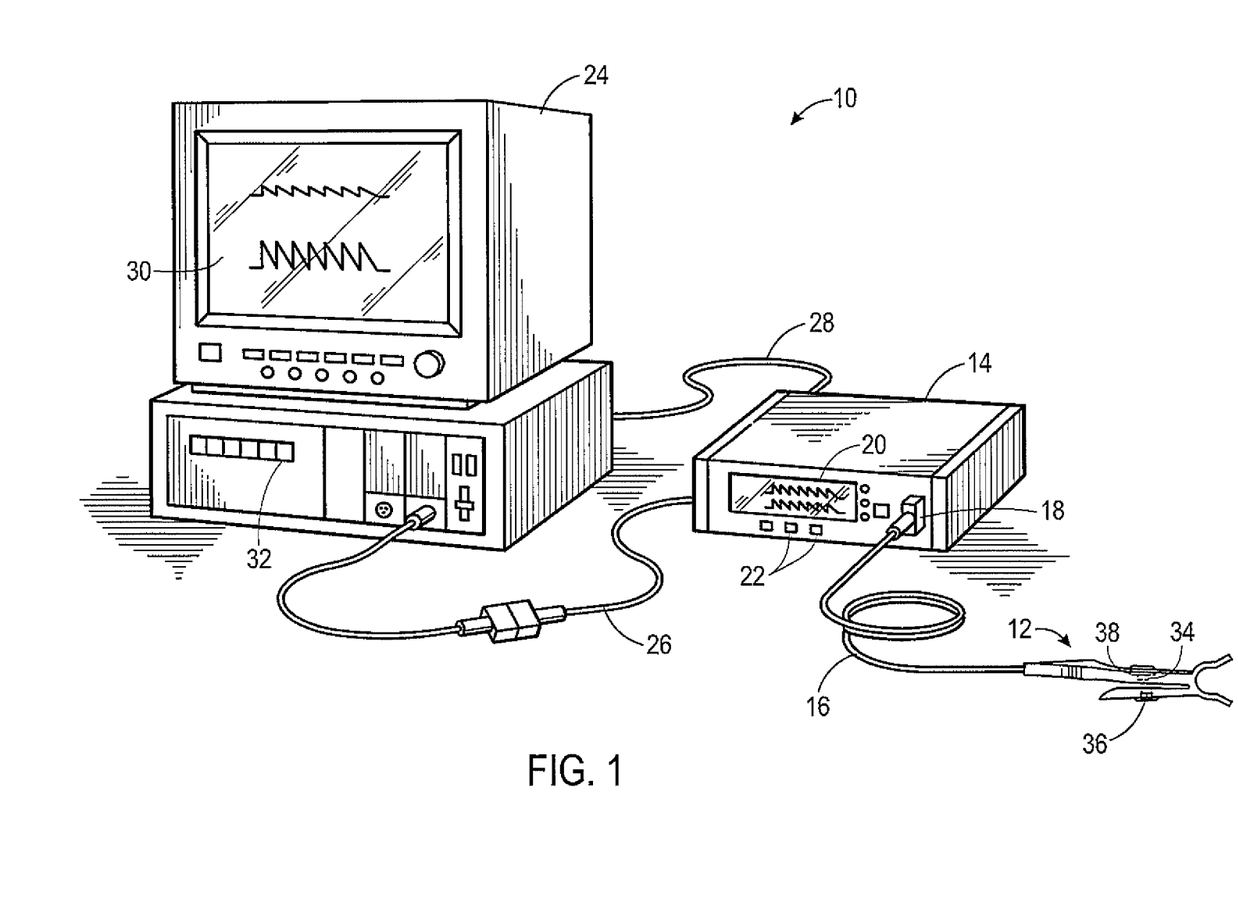
FIG. 1 is a perspective view of a medical monitoring system system that includes a sensor with temperature control, in accordance with certain embodiments.

With the foregoing considerations in mind, FIG. 1 depicts a medical monitoring system, such as a pulse oximetry system 10, having a sensor 12 coupled to a monitor 14 in accordance with an embodiment of the present disclosure. The sensor 12 may be coupled to the monitor 14 via a sensor cable 16 and a sensor connector 18, or the sensor 12 may be coupled to a transmission device (not shown) to facilitate wireless transmission between the sensor 12 and the monitor 14. The monitor 14 may be any suitable monitor, such as those available from Nellcor Puritan Bennett L.L.C., of Boulder, Colo. The monitor 14 may be configured to calculate physiological parameters from signals received from the sensor 12 when the sensor 12 is placed on a patient. For example, the monitor 14 may be configured to determine physiological characteristics, such as the blood-oxygen saturation of hemoglobin in arterial blood, the volume of individual blood pulsations supplying the tissue, and/or the rate of blood pulsations corresponding to each heartbeat of a patient. Further, in certain embodiments, the monitor 14 may be configured to determine additional physiological parameters, such as respiratory rate, respiratory effort, continuous non-invasive blood pressure, cardiovascular effort, glucose levels, level of consciousness, total hematocrit, hydration, electrocardiography, temperature, or any other suitable physiological parameter.

The monitor 14 may include a display 20 configured to display information regarding the physiological parameters, information about the system, and/or alarm indications. For example, the display 20 may be configured to display computed physiological data such as an oxygen saturation percentage, a pulse rate, and/or a plethysmographic waveform. The monitor 14 also may include various input components 22, such as knobs, switches, keys and keypads, buttons, etc., to provide for operation and configuration of the monitor.

In certain embodiments, the monitor 14 may be coupled to a multi-parameter patient monitor 24 to provide additional functionality. For example, the monitor 14 may be connected to the multi-parameter patient monitor 24 via a cable 26 connected to a sensor input port or via a cable 28 connected to a digital communication port. In addition to the monitor 14, or alternatively, the multi-parameter patient monitor 24 may be configured to calculate physiological parameters and to provide a central display 30 for information from the monitor 14 and from other medical monitoring devices or systems. In some embodiments, the monitor 24 may be configured to display and/or determine some or all of the same physiological parameters as monitor 14. The monitor 24 also may include various input components 32, such as knobs, switches, keys and keypads, buttons, etc., to provide for operation and configuration of the monitor 24. Further, the monitor 14 and/or the multi-parameter patient monitor 24 may be connected to a network to enable the sharing of information with servers or other workstations.

The sensor 12 may be any sensor suitable for detection of any physiological parameter. According to certain embodiments, the sensor 12 may be configured for photoelectric detection of blood and tissue constituents. For example, the sensor 12 may be a pulse oximetry sensor, such as those available from Nellcor Puritan Bennett, L.L.C. The sensor 12 may include an emitter 34 for emitting light at certain wavelengths into a patient's tissue and a detector 36 for detecting the light after it is reflected and/or absorbed by the patient's tissue. The sensor 12 also may include a temperature control element 38 for controlling the temperature of light sources in the emitter 34, as discussed further below with respect to FIG. 2. Further, the sensor 12 may include additional components, such as acoustic transducers or microphones, electrodes for measuring electrical activity or potentials (such as for electrocardiography), pressure sensors, motion sensors, and temperature sensors, among others.

As shown in FIG. 1, the sensor 12 may be a clip-type sensor suitable for placement on an appendage of a patient, e.g., a digit, an ear, etc. In other embodiments, the sensor 12 may be a bandage-type sensor having a generally flexible sensor body to enable conformable application of the sensor to a sensor site on a patient. In yet other embodiments, the sensor 12 may be secured to a patient via adhesive (e.g., in an embodiment having an electrode sensor) on the underside of the sensor body or by an external device, such as headband or other elastic tension device. In yet other embodiments, the sensor 12 may be a configurable sensor capable of being configured or modified for placement at different sites (e.g., multiple tissue sites, such as a digit, a forehead of a patient, etc.). The sensor 12 may be a transmittance types sensor or a reflectance type sensor, as described further below with respect to FIG. 3. Further, in certain embodiments, the system 10 may include multiple sensors instead of the single sensor 12.

Figure 2:
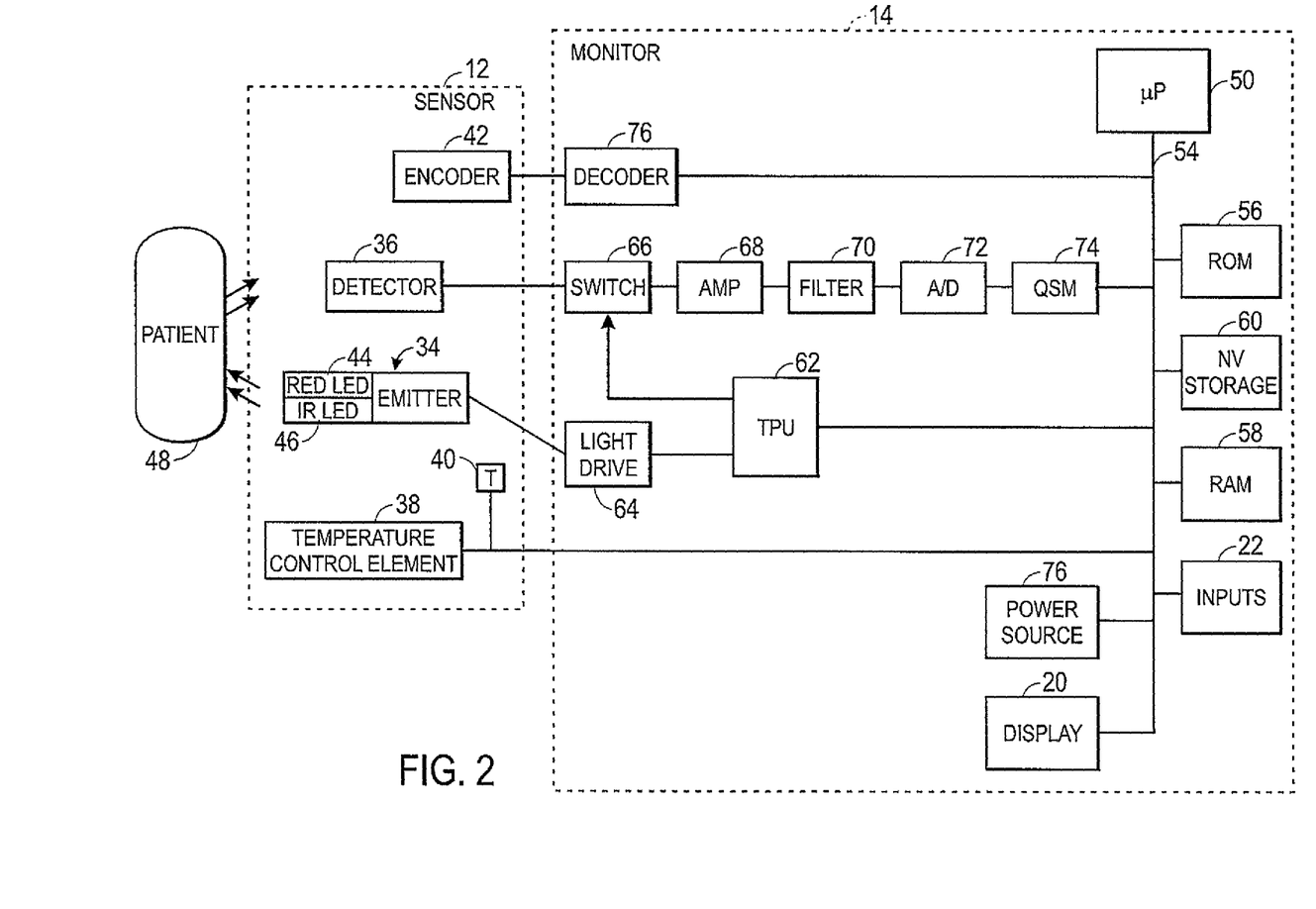
FIG. 2 is a block diagram of the medical monitor and sensor of FIG. 1, in accordance with certain embodiments.

Turning to FIG. 2, a simplified block diagram of a portion of the medical monitoring system 10 is illustrated, in accordance with certain embodiments. Specifically, certain components of the sensor 12 and the monitor 14 are illustrated in FIG. 2. The sensor 12 includes the emitter 34, the detector 36, and the temperature control element 38, as well a temperature sensor 40 and an encoder 42. The emitter 34 includes two light sources 44 and 46, shown here as LEDs, that are capable of emitting different wavelengths of light into the tissue of a patient 48 to measure physiological parameters of the patient 48. As shown in FIG. 2, the light source 44 represents a red LED designed to emit red light at a wavelength between about 600 nanometers (nm) and about 700 nm, and the light source 46 represents an infrared (IR) LED designed to emit IR light at a wavelength between about 800 nm and about 1000 nm. However, in other embodiments, the light sources 44 and 46 may be designed to emit light at other suitable wavelengths.

Although two light sources are shown in FIG. 2, in other embodiments, any number of one or more light sources can be included in the emitter 34. For example, in certain embodiments, the emitter 34 may include three light sources: a red light source designed to emit light red light at a wavelength between about 620 nm and about 700 nm, a far red light source designed to emit far red light at a wavelength between about 690 nm and about 770 nm, and an infrared light source designed to emit infrared light at a wavelength between about 860 nm and 940 nm. In these embodiments, different combinations of light sources may be used to measure physiological parameters depending on the current arterial oxygen saturation value. For example, when blood perfused tissue has a high arterial oxygen saturation value (e.g., greater than 84%), the $SpO_2$ value may be more accurately calculated by employing the red light source and the infrared light source. On the other hand, when blood perfused tissue has a low arterial oxygen saturation value (e.g., less than 75%), the $SpO_2$ value may be more accurately calculated by employing the far red light source and the infrared light source. When the blood perfused tissue has an intermediate arterial oxygen saturation value (e.g., between 75% and 84%), measurements may be taken using the red and infrared light sources, the near red and infrared light sources, or a combination of the red, near red, and infrared light sources (e.g., readings from the light sources may be averaged and/or weighted). In these embodiments, the light sources that are used may be selected based on a previously measured arterial oxygen saturation value. According to certain embodiments, the sensor 12 may include a three wavelength emitter, or set of emitters, such as those described in U.S. patent application Ser. No. 12/888, 226, entitled "Wavelength Switching for Pulse Oximetry," which is herein incorporated by reference.

It should be understood that, as used herein, the term "light" may refer to one or more of ultrasound, radio, microwave, millimeter wave, infrared, visible, ultraviolet, gamma ray or X-ray electromagnetic radiation, and may also include any wavelength within the radio, microwave, infrared, visible, ultraviolet, or X-ray spectra, and that any suitable wavelength of light may be appropriate for use with the present disclosure. In operation, light enters the detector 36 after passing through the tissue of the patient 48. The detector 36 may convert the light at a given intensity, which may be directly related to the absorbance and/or reflectance of light in the tissue of the patient 48, into an electrical signal. That is, when more light at a certain wavelength is absorbed or reflected, less light of that wavelength is typically received from the tissue by the detector 36. For example, the detector 36 may include one or more photodiodes, or any other element capable of converting light into either a current or voltage. After converting the received light to an electrical signal, the detector 36 may send the signal to the monitor 14, where physiological characteristics may be calculated based at least in part on the absorption of light in the tissue of the patient 48.

The sensor 12 also includes the temperature control element 38 and the temperature sensor 40, which can be used to regulate the temperature of the emitter 34 and its light sources 44 and 46. The temperature sensor 40 may be any device suitable for measuring temperature, such as a thermistor or thermocouple, among others. The temperature sensor 40 may be located in close proximity to the emitter 34 or may be coupled to the emitter 34 in order to detect the temperature of the light sources 44 and 46. The temperature control element 38 may include one or more elements designed to provide heating and/or cooling. For example, the temperature control element 38 may be a thermoelectric element that is switchable between a cooling mode to provide cooling and a heating mode to provide heating. In another example, the temperature control element 38 may include a thermoelectric cooler that provides cooling and a resistive heater that provides heating. Further, in yet other embodiments, the temperature control element 38 may be designed to provide only heating or only cooling. The temperature control element 38 may be disposed in close proximity to the light sources 44 and 46 or may be coupled to the light sources 44 and 46 and/or the emitter 34 to provide heating and/or cooling to the light sources 44 and 46.

The temperature control element 38 and the temperature sensor 40 can be used in conjunction with one or more processors 50 of the monitor 14 to provide closed loop control of the temperature of the light sources 44 and 46. In particular, the temperature control element 38 may be used to maintain the temperature of light sources 44 and 46 at a target temperature set point or within a target temperature range. Because the wavelengths emitted by the light sources 44 and 46 can vary with temperature, the target temperature set point may be selected to correspond to a desired wavelength of light. For example, as discussed further below with respect to FIG. 8, the target temperature set point may correspond to a temperature that allows the light sources 44 and 46 to produce wavelengths that correspond to a calibration profile included in the monitor 14. In another example, as discussed further below with respect to FIG. 9, the target temperature set point may be used to shift the wavelengths emitted by the light sources in order to measure certain physiological parameters, such as total hemoglobin, or to shift the wavelengths to provide increased accuracy in the measurements. Further, the temperature control element 38 can be employed to provide temperature adjustments that compensate for changes in the ambient temperature and/or the operational temperature of the light sources 44 and 46.

The sensor 12 also includes the encoder 42, which contains information about the sensor 12, such as the sensor type (e.g., whether the sensor is intended for placement on a forehead, digit, or other body part) and the wavelengths of light emitted by the light sources 44 and 46. The sensor information may allow the monitor 14 to select appropriate algorithms and/or calibration coefficients for calculating the physiological characteristics of the patient 48. Further, the information may be used by the monitor 14 to determine a target temperature set point and/or target temperature range for the light sources 44 and 46. According to certain embodiments, the encoder 42 may include a memory on which one or more of the following information may be stored for communication to the monitor 14: the type of the sensor 12; the wavelengths of light emitted by the light sources 44 and 46; and the proper calibration coefficients and/or algorithms to be used for calculating the physiological characteristics of the patient 48.

Signals from the encoder 42 can be transmitted to a detector/decoder 52 in the monitor 14 where the data and signals can be decoded. The detector/decoder 52 may decode the signals from the encoder 42 and may provide the decoded information to the processor 50. According to certain embodiments, the decoded information may represent the type of the sensor 12 and the wavelengths of light emitted by the light sources 44 and 46. The processor 50 may then use the decoded information to determine the proper method for calculating the patient's physiological characteristics. For example, the processor may use the decoded information in conjunction with algorithms or look-up tables to identify the proper calibration coefficients and/or algorithms to be used for calculating the patient's physiological characteristics.

Signals from the detector 36 also may be transmitted to the monitor 14 where the signals can be used to calculate the patient's physiological characteristics. The monitor 14 generally includes the one or more processors 50 connected to an internal bus 54. The bus 54 is also connected to the input components 22 and the display 20, as well as a read-only memory (ROM) 56, a random access memory (RAM) 58, and a nonvolatile storage 60 (such as a magnetic or solid state hard drive or memory, optical disk, or any other suitable optical, magnetic, or solid-state computer readable media) that stores longer-term data.

A time processing unit (TPU) 62 may provide timing control signals to a light drive circuitry 64, which controls when the emitter 34 is illuminated and the multiplexed timing for the light sources 44 and 46. The TPU 62 also may control the gating-in of signals from detector 36 through a switching circuit 66. These signals may be sampled at the proper time, depending upon which light source 44 or 46 is illuminated. The received signal from the detector 36 may be passed through an amplifier 68, a low pass filter 70, and an analog-to-digital converter 72 for amplifying, filtering, and digitizing the electrical signals the from the sensor 12. The digital data may then be stored in a queued serial module (QSM) 74 for later downloading to the RAM 58 as the QSM 74 fills up. In certain embodiments, there may be multiple separate parallel paths having the amplifier 68, the filter 70, and the A/D converter 72 for multiple light wavelengths or spectra received.

The processor 50 may use the digital data, as well as other signals from the detector 36 to calculate and/or determine physiological characteristics, such as oxygen saturation, pulse rate, and total hemoglobin, among others. For example, the processor 50 may use various encoded instructions, algorithms, and/or lookup tables that may be stored in the ROM 56, as well as in the nonvolatile storage 60, to calculate the physiological characteristics based at least in part upon the signals that correspond to the light received by the detector 36. According to certain embodiments, code encoding executable algorithms may be stored in the ROM 56 or the nonvolatile storage 60 and accessed and operated according to processor instructions. The calculated physiological characteristic may then be displayed on the display 20 for a caregiver to monitor or review. In certain embodiments, the processor 50 also may access and execute coded instructions for adjusting the temperature of the light sources 44 and 46 using the temperature control element 38. According to certain embodiments, one or more algorithms and/or lookup tables may be stored in the ROM 56 or the nonvolatile storage 60 and employed by the processor 50 to adjust the temperature of the light sources 44 and 46.

The monitor 14 further includes a power source 76 that may be used to transmit power to the components located in the monitor 14 and/or the sensor 12. In one embodiment, the power source 76 may be one or more batteries, such as a rechargeable battery. The battery may be user-removable or may be secured within the housing of the monitor 14. Use of a battery may, for example, allow the monitor 14 to be highly portable, thus allowing a user to carry and use the monitor 14 in a variety of situations and locations. Additionally, the power source 76 may include AC power, such as provided by an electrical outlet, and the power source 76 may be connected to the AC power via a power adapter through a power cord (not shown). This power adapter may also be used to directly recharge one or more batteries of the power source 76 and/or to power the monitor 14.

The power source 76 also may provide power to the temperature control element 38 within the sensor 12. According to certain embodiments, the power source 76 may include DC power that can be provided to the temperature control element 38, For example, the power source 76 may include an AC/DC converter that converts AC power provided by an electrical outlet to DC power. According to certain embodiments, the level of power provided to the temperature control element 38 may determine the amount of heating and/or cooling generated by the temperature control element 38. For example, in embodiments where the temperature control element 38 includes a thermoelectric element, the amount of cooling and/or heating provided may be proportional to the applied current. According to certain embodiments, the processor 50 may control the level of power provided to the temperature control element 38 from the power source 76. For example, the processor 50 may employ one or more algorithms and/or instructions stored in the ROM 56 or the nonvolatile storage 60 to determine the level of power that should be provided to the temperature control element 38. Further, in certain embodiments, the processor 50 may employ linear control or pulse width modulation (PWM) control to govern the level of power provided to the temperature control element 38. As discussed further below with respect to FIG. 7, the processor 50 may receive temperature data over the bus 54 from the temperature sensor 40. Based on the detected temperature, the processor 50 may adjust operation of the temperature control element 38 to maintain the temperature of the light sources 44 and 46 at a target temperature set point or within a target temperature range.

Figure 3:
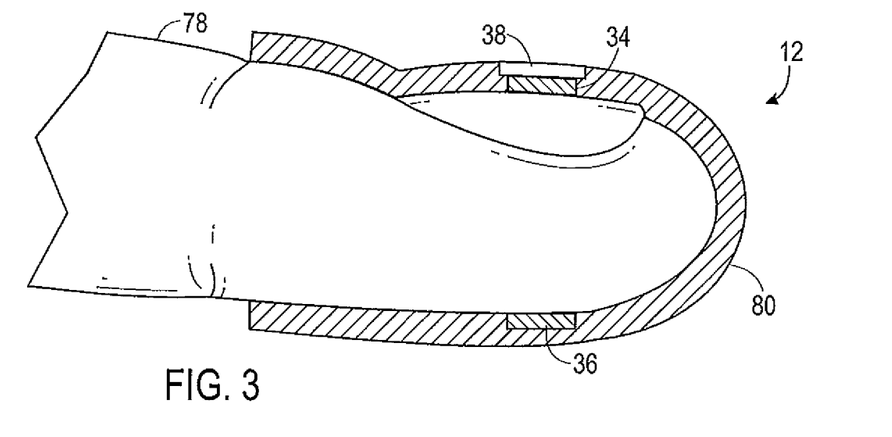
FIG. 3 is a cross-sectional view of the sensor of FIG. 1 attached to a patient, in accordance with certain embodiments.

FIG. 3 illustrates the location of the temperature control element 38 within the sensor 12. As shown in FIG. 3, the sensor 12 is disposed on a patient's finger 78. However, in other embodiments, the sensor may be affixed to a patient's finger, toe, foot, ear, or forehead, among others. The sensor 12 includes a housing 80 that contains the emitter 34 and the detector 36. As shown in FIG. 3, the emitter 34 and the detector 36 are arranged in a transmittance type configuration where the emitter 34 and the detector 36 are located on opposite sides of the patient's finger 78. In this configuration, light from the emitter 34 passes through the vascularized tissue of the patient's finger 78 to reach the detector 36 on the other side of the tissue. However, in other embodiments, the sensor may have a reflectance type configuration where the emitter 34 and the detector 36 are positioned on the same side of the vascularized tissue so that light from the emitter 34 is reflected through the tissue underneath the emitter 34 and back into the detector 36.

The temperature control element 38 is located within the housing 80 in close proximity to the emitter 34 so that heat can be exchanged between the temperature control element 38 and the emitter 34. As discussed above with respect to FIG. 2, the temperature control element 38 may be employed to maintain the emitter 34 and light sources 44 and 46 at a desired temperature, or range of temperatures, in order to regulate the wavelengths of light emitted by the emitter 34. According to certain embodiments, the temperature control element 38 can be directly coupled to a surface of the emitter 34. However, in other embodiments, the temperature control element 38 may be placed in close proximity to the emitter 34 and a thermally conductive material may be disposed between the emitter 34 and the temperature control element 38.

The temperature control element 38 may be disposed on the opposite side of the emitter 34 from the finger 78. Accordingly, when the temperature control element 38 is providing cooling, heat can be transferred from the emitter 34 to the temperature control element 38 and then released to the ambient air surrounding the sensor 12. In certain embodiments, a portion of the housing 80 may be omitted in the region adjacent to the temperature control element 38 to allow the temperature control element 38 to directly contact the ambient air. However, in other embodiments, at least a portion of the housing 80 that surrounds the temperature control element 38 may include a thermally conductive material that allows heat to be transferred from the temperature control element 38 through the housing to the ambient air.

Figure 4:
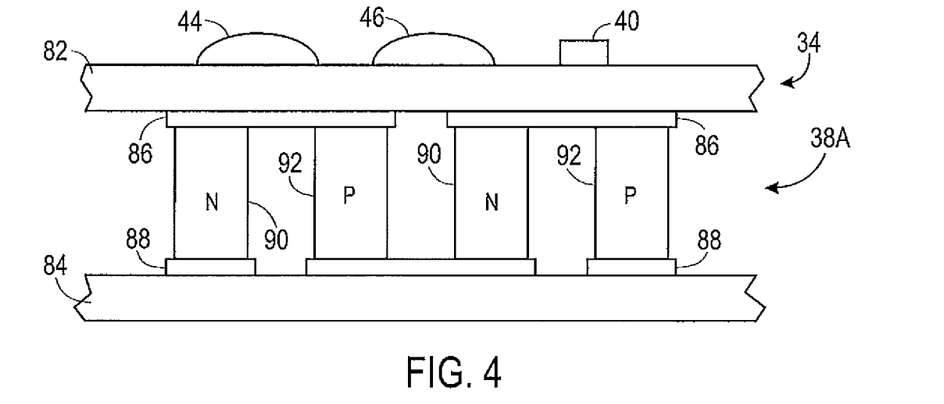
FIG. 4 is a schematic diagram of an embodiment of a temperature control element that can be employed in the sensor of FIG. 1, in accordance with certain embodiments.
Figure 5:
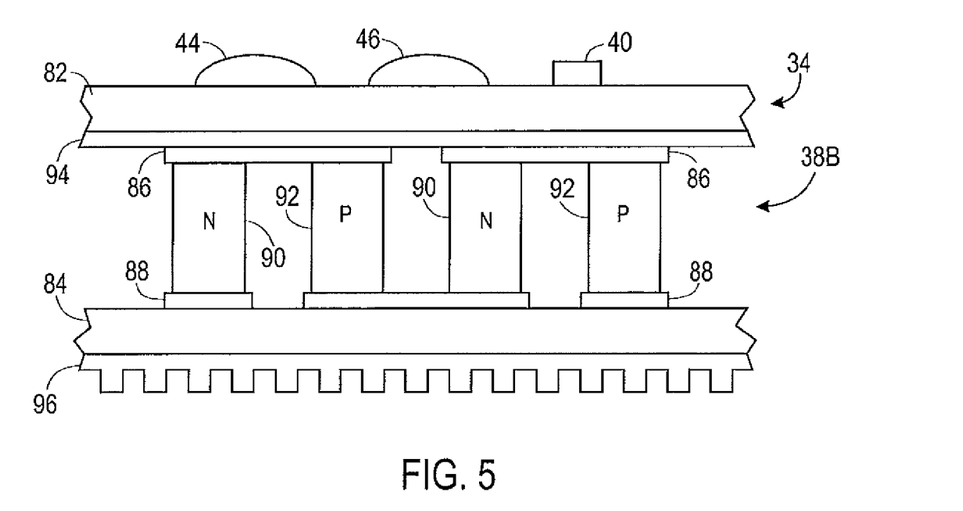
FIG. 5 is a schematic diagram of another embodiment of a temperature control element that can be employed in the sensor of FIG. 1, in accordance with certain embodiments.
Figure 6:
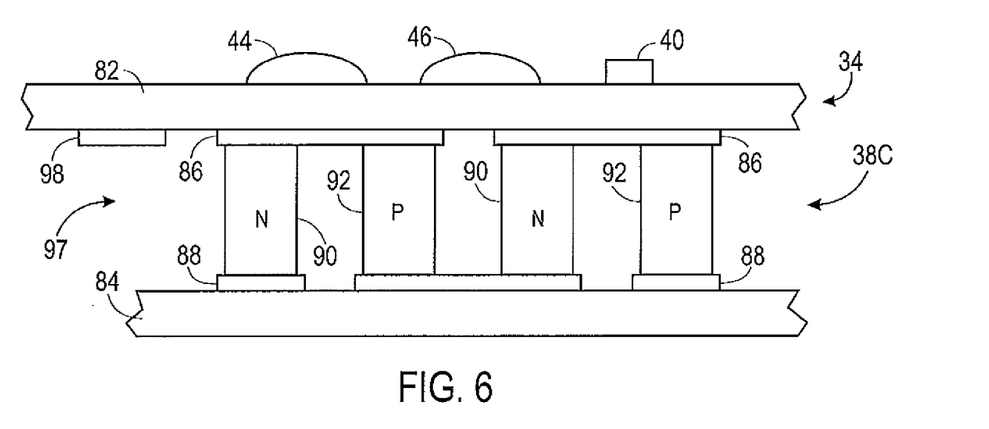
FIG. 6 is a schematic diagram of another embodiment of a temperature control element that can be employed in the sensor of FIG. 1, in accordance with certain embodiments.

FIGS. 4 to 6 depict embodiments of temperature control elements 38A, 38B, and 38C coupled to the emitter 34. As shown in FIG. 4, the emitter 34 includes the light sources 44 and 46, which are disposed on a substrate 82. According to certain embodiments, the substrate 82 may include internal circuitry that provides signals and power from the light drive 64 (FIG. 2) to the light sources 44 and 46. In certain embodiments, the substrate 82 may be an electrically insulating and thermally conducting material, such as a ceramic. The temperature sensor 40 also may be mounted to the substrate 82 to detect the temperature of the light sources 44 and 46. As shown, a single temperature sensor 40 is included to detect the temperature of the light sources 44 and 46. However, in other embodiments, multiple temperature sensors may be employed and, in certain embodiments, the temperature of each light source 44 and 46 may be detected by individual temperature sensors. Further, in certain embodiments, additional temperature sensors may be included in the sensor 12 to measure the ambient air temperature and/or the temperature of the patient's skin.

As shown in FIG. 4, the temperature control element 38A is disposed below and slightly to the right of center with respect to the light sources 44 and 46, and the temperature sensor 40 is disposed on the substrate 82 to the right of the light sources 44 and 46. In other embodiments, the location of the temperature control element 38A and/or the temperature sensor 40 with respect to the light sources 44 and 46 may vary, depending on factors, such as the particular design of the sensor 12, among others. For example, the temperature control element 38A may be centered directly underneath the light sources 44 and 46 or positioned to the left or right of center with respect to the light sources 44 and 46. In another example, the temperature sensor 40 may be located between the light sources 44 and 46. Moreover, in certain embodiments, multiple temperature control elements 38A may be included in the sensor 12. Further, in certain embodiments, thermal modeling may be employed to optimize the location of the temperature control element 38A and/or the temperature sensor 40, as well as to optimize the number of temperature control elements 38A and/or temperature sensors 40 that are included in the sensor 12.

In the embodiment shown in FIG. 4, the temperature control element 38A represents a thermoelectric element capable of both cooling and heating. The temperature control element 38A includes a substrate 84 that may be an electrically insulating and thermally conducting material, such as a ceramic. Conductive layers 86 and 88 are coupled to the substrates 82 and 84, respectively. The conductive layers 86 and 88 may include gold, aluminum, or copper, or combinations thereof, as well as any other electrically conductive material. For example, in certain embodiments, the conductive layers 86 and 88 may be patterned electrode layers of gold titanium or copper titanium. Leads may be attached to the conductive layers 86 and 88 and connected to the power source 76 to direct current through the conductive layers 86 and 88 and transfer heat through thermoelectric materials 90 and 92 that are disposed between the conductive layers 86 and 88.

According to certain embodiments, the thermoelectric materials 90 and 92 may include semiconductor materials, such as semiconductor pellets of bismuth telluride or other suitable materials. The thermoelectric material 90 is an N-type thermoelectric material, while the thermoelectric material 92 is P-type thermoelectric material. The thermoelectric materials 90 and 92 may be doped by introducing impurities into the thermoelectric materials 90 and 92 to change their electrical properties. For example, the thermoelectric material 90 may be doped by introducing an impurity with a surplus of electrons to generate an N-type thermoelectric material. Similarly, the thermoelectric material 92 may be doped by introducing an impurity with a surplus of free charge carriers (holes) to generate a P-type thermoelectric material.

The thermoelectric materials 90 and 92 are electrically coupled in series and thermally coupled in parallel. Further, the thermoelectric materials 90 and 92 are alternately arranged between the conductive layers 86 and 88. Accordingly, when current is applied to the conductive layers 86 and 88, heat may be transferred from one side of temperature control element 38A to the other side of temperature control element 38A. In particular, heat may be transferred from one substrate 82 or 84, to the other substrate 84 or 82.

According to certain embodiments, temperature control element 38A includes a bipolar controller with switches that allow the direction of current flow through temperature control element 38A to be reversed. Accordingly, current may be directed through temperature control element 38A in a first direction to provide cooling where heat is transferred from substrate 82 to substrate 84 to cool the emitter 34 and light sources 44 and 46. Further, current may be directed through temperature control element 38A in an opposite direction to provide heating where heat is transferred from substrate 84 to substrate 82 to heat the emitter 34 and light sources 44 and 46. In other words, the direction of current flow determines which substrate 82 or 84 of temperature control element 38A is the hot end and which end is the cool end. Further, according to certain embodiments, the amount of current applied to the temperature control element 38A determines the amount of cooling and heating that is provided. Accordingly, to adjust the level of heating and cooling, the processor 50 (FIG. 2) may alter the level of power that is provided to the temperature control element 38A.

According to certain embodiments, the processor 50 may transmit control signals to the temperature control element 38A to control the direction of current flow through temperature control element 38A, and to thereby determine whether the temperature control element 38A provides heating or cooling. In the cooling mode, heat from the emitter 34 may be transferred to substrate 82 to cool light sources 44 and 46. The heat from substrate 82 may then be transferred through the thermoelectric materials 90 and 92 to the substrate 84. The heat that is transferred to substrate 84 may be released to the ambient air surrounding the sensor 12. In the heating mode, heat may be transferred from the ambient air to the substrate 84. The heat from the substrate 84 may then be transferred through the thermoelectric materials 90 and 92 to the substrate 82 where the heat may be provided to the emitter 34 to increase the temperature of the light sources 44 and 46.

FIG. 5 depicts another embodiment of a temperature control element 38B. The temperature control element 38B is generally similar to the temperature control element 38A and includes the conductive layers 86 and 88, the substrate 84, and the thermoelectric materials 90 and 92. However, the temperature control element 38B also includes an additional substrate 94. The substrate 94 may include an electrically insulating and thermally conductive material, such as a ceramic, and may facilitate attachment of the temperature control element 38B to the emitter 34. For example, the substrate 94 may be affixed by soldering, adhesive, or mechanical mounting, to the substrate 82. According to certain embodiments, the inclusion of the substrate 94 may facilitate manufacturing and/or assembly by allowing the temperature control element 38B to be attached to the emitter 34 as a single piece. The temperature control element 38B also may include an optional heat sink 96 that increases the surface area for heat transfer between the substrate 84 and the ambient air. However, in other embodiments, the heat sink 96 may be omitted.

FIG. 6 depicts yet another embodiment of a temperature control element 38C. In this embodiment, the temperature control element 38C includes a thermoelectric cooler 97 that provides cooling, but does not provide heating. Accordingly, current may flow through the thermoelectric cooler 97 in a single direction to transfer heat from the substrate 82 to the substrate 84. To provide heating, a heating element, such as a resistive heater 98 may be affixed to the substrate 82. The resistive heater 98 may receive current from the power source 76 (FIG. 2) to provide heat to the substrate 82, and consequently to the emitter 34 and the light sources 44 and 46. However, in other embodiments, the resistive heater and 98 may be omitted and the temperature control element 38C may be configured to provide only cooling. Further, in other embodiments, the thermoelectric cooler 97 may be omitted and the temperature control element 38C may be configured to provide only heating.

Figure 7:
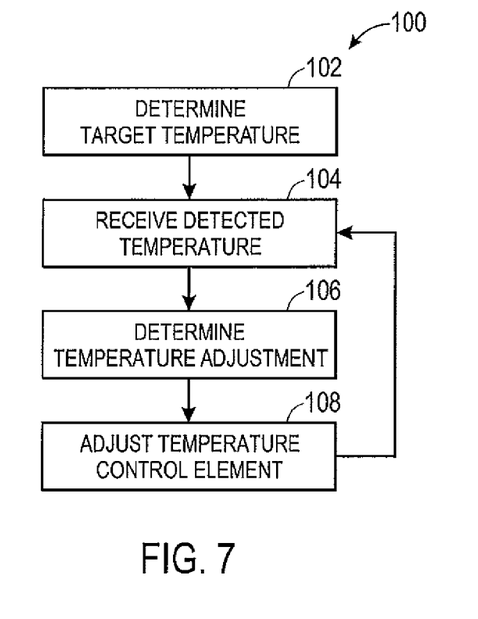
FIG. 7 is a method that can be employed to control the temperature of the sensor of FIG. 1, in accordance with certain embodiments.

FIG. 7 depicts a method 100 that can be employed to control the temperature of the light sources 44 and 46 to a target temperature. The target temperature may represent a specific temperature value or may represent a specific range of temperatures. As discussed below with respect to FIG. 8, the target temperature may represent a temperature that allows the light sources 44 and 46 to emit wavelengths that correspond to a calibration profile included within the monitor 14. Further, as discussed below with respect to FIG. 9, the target temperature may represent a temperature that allows the light sources 44 and 46 to emit adjusted wavelengths that can be used to determine other physiological parameters, such as total hemoglobin. In these embodiments, a single light source 44 or 46 can be used to emit multiple wavelengths.

Regardless of the target temperature, the method 100 may be employed to maintain the temperature of the light sources 44 and 46 at the target temperature even during ambient temperature changes and/or operational temperature changes. For example, if the sensor 12 loses full contact with a patient's finger 78, a low signal to noise ratio may result, and the light sources 74 and 76 may be driven harder. The increased driving strength may increase the temperature of the emitter 34, and accordingly, additional cooling may be desired to cool the light sources 44 and 46, as well as the patient's skin. In another example, when the light drive 64 is operating at a low pulse width modulation (PWM), the temperature produced by the emitter 34 may decrease relative to higher PWM's. In this situation, the temperature control element 38 may be employed to provide heating to maintain the emitter 34 at the desired temperature, and thereby ensure that the light sources 44 and 46 emit the desired wavelengths. In summary, the method 100 may be employed to maintain the light sources 44 and 46 at the target temperature, which in turn, ensures that the desired wavelengths are emitted by the light sources 44 and 46.

The method 100 may begin by determining (block 102) the target temperature. The target temperature may be retrieved from the ROM 56 or from the nonvolatile storage 60 and may correspond to the temperature that the light sources 44 and 46 should be maintained at in order to emit the desired wavelengths. According to certain embodiments, the processor 50 may execute encoded instructions to determine the target temperature that allows the light sources 44 and 46 to emit the desired wavelengths. For example, as discussed further below with respect to FIG. 8, the processor 50 may determine a target temperature that allows the light sources 44 and 46 to emit wavelengths corresponding to a calibration profile. In another example, as discussed further below with respect to FIG. 9, the processor 50 may determine a target temperature that allows the light sources 44 and 46 to emit adjusted wavelengths for determining certain physiological parameters. The light sources 44 and 46 may have a shared target temperature or each light source 44 and 46 may have a separate target temperature.

The processor 50 may then receive (block 104) the detected temperature of the light sources 44 and 46. For example, the temperature sensor 40 may detect the temperature of the light sources 44 and 46 and provide data representing the detected temperature to the processor 50. The processor 50 may then determine (block 106) a temperature adjustment based on the detected temperature and the target temperature. For example, the processor 50 may compare the detected temperature to the target temperature and determine the amount and direction of temperature adjustment that is needed to align the temperature of the light source 44 and/or 46 with the target temperature. According to certain embodiments, the processor 50 may employ one or more algorithms or lookup tables to determine the direction and amount of the temperature adjustment.

The processor 50 may then adjust (block 108) operation of the temperature control element to achieve the determined temperature adjustment. For example, the processor 50 may adjust a level of power provided to the temperature control element 38 to increase or decrease the level of heating or cooling provided by the temperature control element 38.

According to certain embodiments, the processor 50 may transmit control signals to the power source 76 or to the temperature control element 38 over the bus 54 to adjust the level of power provided to the temperature control element 38. Further, in embodiments where the temperature control element 38 is capable of providing both heating and cooling, the processor 50 may switch the temperature control element 38 between a heating and a cooling mode. For example, as shown in FIGS. 4 and 5, the processor 50 may transmit a control signal to the temperature control element 38A or 38B to reverse the direction of current flow through the temperature control element. In embodiments where the temperature control element 38 includes separate heating and cooling elements, the processor 50 may determine which temperature control element is operational. For example, as shown in FIG. 6, the processor 50 may transmit a control signal to the temperature control element 38C to determine whether the thermoelectric cooler 97 should provide cooling or whether the resistive heater 98 should provide heating. According to certain embodiments, the control signal may determine whether power is applied to the thermoelectric cooler 97 or to the resistive heater 98.

After the operation of the temperature control element has been adjusted (block 108), the processor 50 may again receive (block 104) the detected temperature and determine (block 106) a temperature adjustment. According to certain embodiments, the method 100 may be repeated continuously or at set intervals to maintain the temperature of the light sources 44 and 46 at the target temperature. Further, as may be appreciated, a certain amount of hysteresis may be employed when adjusting operation of the temperature control element 38. For example, in certain embodiments, the processor 50 may adjust operation of the temperature control element 38 after detecting a threshold amount of change in the temperature of the light sources 44 and 46.

Figure 8:
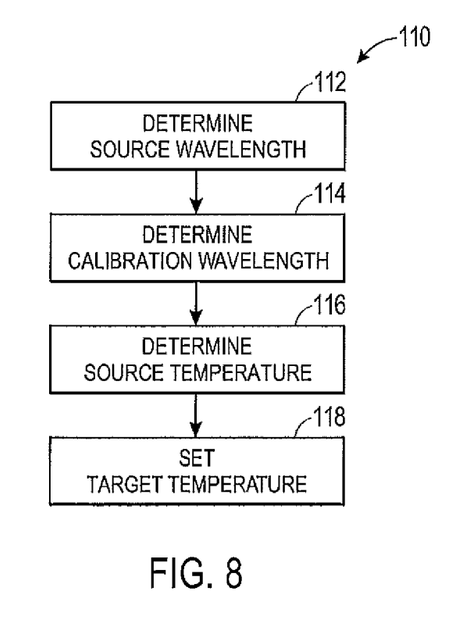
FIG. 8 is a method that can be employed to calibrate the sensor of FIG. 1 to a desired wavelength, in accordance with certain embodiments.

FIG. 8 depicts a method 110 that can be employed to determine a target temperature for the light sources 44 and 46. According to certain embodiments, the method 110 may be employed to align the wavelengths of the light sources 44 and 46 with a calibration profile included within the monitor 14. Due to manufacturing variations, the peak wavelengths of individual light sources 44 and 46 may vary. Accordingly, different sensors 12 may include light sources 44 and 46 of slightly different wavelengths. The method 110 may be employed to vary the temperature of the light sources 44 and 46 so that the wavelengths emitted by the light sources match a calibration profile included within the monitor 14.

The method 110 may begin by determining (block 112) the wavelengths for the light sources included in the emitter. For example, data indicative of the wavelengths of the light sources 44 and 46 may be stored within the encoder 42, The data from the encoder 42 may then be provided to the decoder 52 in the monitor 14 and may be stored within the ROM 56 or the nonvolatile storage 60. The processor 50 may the retrieve this data from the ROM 56 or the non-volatile storage 60.

The method 100 may then continue by determining (block 114) the calibration wavelengths. For example, a calibration profile including one or more calibration curves and/or algorithms for calculating physiological parameters may be stored within the ROM 56 or the nonvolatile storage 60. The calibration profile may be designed to perform calculations using light sources 44 and 46 that operate at specific wavelengths. These specific wavelengths may be stored within the ROM 56 or the non-volatile storage 60. The processor 50 may then retrieve these wavelengths from the ROM 56 or the nonvolatile storage 60.

The processor 50 may then determine (block 116) a temperature for the light sources 44 and 46 that allows the light sources 44 and 46 to emit light at wavelengths corresponding to the calibration wavelengths. For example, if the peak wavelengths of the light sources 44 and 46 are greater than the calibration wavelengths, a temperature that is higher than the suggested operating temperature for the light sources 44 and 46 may be selected to decrease the wavelengths emitted by the light sources 44 and 46. Similarly, if the peak wavelengths of the light sources 44 and 46 are lower than the calibration wavelengths, a temperature that is lower than the suggested operating temperature for the light sources 44 and 46 may be selected to increase the wavelengths emitted by the light sources 44 and 46. By comparing the light source peak wavelengths to the calibration wavelengths, the processor 50 may determine whether the temperature of the light sources 44 and 46 should be increased or decreased to match the emitted wavelengths to the calibration wavelengths. The processor 50 also may determine the amount by which the temperature should be increased or decreased. For example, the processor 50 may employ one or more algorithms or lookup tables stored in the ROM 56 or the nonvolatile storage 60 to determine the target temperature for the light sources 44 and 46. After determining the target temperature, the processor 50 may then set (block 118) the target temperature for the light sources 44 and 46. For example, the processor 50 may store the target temperature within the ROM 56 or the nonvolatile storage 60. The stored target temperature may then be employed in the method 100 (FIG. 7) to maintain the light sources 44 and 46 at the target temperature.

Figure 9:
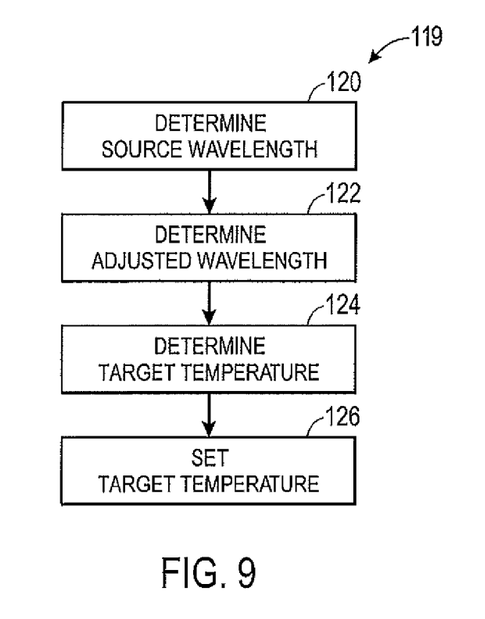
FIG. 9 is a method that can be employed to produce an adjusted wavelength for the sensor of FIG. 1, in accordance with certain embodiments.

FIG. 9 depicts another embodiment of a method 119 that may be employed to determine a target temperature for the light sources 44 and 46. The method 119 may be employed to vary the wavelength emitted by a light source 44 or 46 to allow a single light source 44 or 46 to be used to take measurements at multiple wavelengths. For example, the method 119 may be employed to vary the wavelengths emitted by the light sources 44 and 46 by approximately 40 nm to obtain measurements for calculating total hemoglobin.

Further, in other embodiments, the temperature of the light sources 44 and 46 may be adjusted to emit wavelengths used to determine other physiological parameters such as oxyhemoglobin, carboxyhemoglobin, and methemoglobin, among others. Moreover, in certain embodiments, the method 119 may be employed to vary the wavelength emitted by a light source 44 or 46 based on a current physiological parameter, such as arterial oxygen saturation.

In certain embodiments, the method 119 may be employed to adjust a light source 44 or 46 to emit light at an isosbestic point, where the detected waveform is sensitive to blood volume changes but not to changes in arterial or venous oxygen saturation. For example, the method 119 may be employed to set the wavelength emitted by a light source 44 or 46 to approximately 808 nm, which is an isosbestic point for oxyhemoglobin and de-oxygenated hemoglobin. In other embodiments, the method 119 may be employed to set the emitted wavelength to other isosbestic points, such as an isosbestic point where the absorbance of water and oxyhemoglobin is approximately equal or an isosbestic point where the absorbance of water and de-oxygenated hemoglobin is approximately equal. According to certain embodiments, the method 119 may be employed to adjust a light source 44 or 46 to emit light at a wavelength corresponding to an isosbestic point, and then the method 100 (FIG. 7) may be employed to maintain the wavelength at the isosbestic point.

As shown in FIG. 9, the method 119 may begin by determining (block 120) the peak wavelengths of the light sources 44 and 46. For example, the processor 50 may receive the wavelengths for each light source 44 and 46 from the encoder 42 through the decoder 52. In another example, the processor 50 may retrieve the wavelengths from the ROM 56 or from the nonvolatile storage 60. The processor 50 may then determine (block 122) the desired adjusted wavelength. For example, the processor 50 may determine the wavelength that should be emitted by the light source 44 or 46 to measure the desired physiological characteristics. In another example, the processor 50 may determine the amount of shift from the peak wavelength that should be made to emit light at a wavelength corresponding to a desired isosbestic point. In certain embodiments, the processor 50 may determine the amount of shift from the peak wavelength that should be made to measure the desired physiological characteristics and/or to emit a wavelength corresponding to the desired isosbestic point. According to certain embodiments, the processor 50 may employ one or more algorithms and/or lookup tables stored in the ROM 56 or the nonvolatile storage 60 to determine the adjusted wavelength that corresponds to the physiological parameter to be measured or to the desired isosbestic point.

In certain embodiments, the processor 50 may determine (block 122) a desired adjusted wavelength based on a previously measured physical parameter, such as the level of arterial oxygen saturation. When the arterial oxygen saturation in blood perfused tissue is relatively high (e.g., approximately greater than 84%), the $SpO_2$ value may be more accurately calculated using infrared light paired with light of a relatively low wavelength (approximately 620-700 nm). On the other hand, when the arterial oxygen saturation in blood perfused tissue is relatively low (e.g., less than 75%), the $SpO_2$ value may be more accurately calculated using infrared light paired with light of a relatively higher wavelength (approximately 690-770 nm). Accordingly, it may be desirable to increase the emitted wavelength when the arterial oxygen saturation decreases and to decrease the emitted wavelength when the arterial oxygen saturation increases. One or more previously measured arterial oxygen saturation values may be used to calculate a desired adjusted wavelength. For example, the processor 50 may calculate a desired adjusted wavelength based on an average of previously measured arterial oxygen saturation values, based on a trend in previously measured arterial oxygen saturation values, or based on the most recently measured arterial oxygen saturation value. According to certain embodiments, the processor 50 may employ one or more algorithms and/or lookup tables stored in the ROM 56 or the nonvolatile storage 60 to determine the adjusted wavelength that corresponds to the previously measured arterial oxygen saturation values. According to certain embodiments, the method 119 may be employed to adjust the wavelength emitted by the red light source 44 shown in FIG. 2, or to adjust the wavelengths emitted by a red light source and/or a far red light source within a three wavelength emitter, such as those described in U.S. patent application Ser. No. 12/888,226, as discussed above with respect to FIG. 2.

After determining (block 122) the desired adjusted wavelength, the processor 50 may determine (block 124) the target temperature for producing the desired wavelength. For example, the processor 50 may compare the desired wavelength to the peak wavelength of the light source 44 or 46 and may then determine whether the temperature should be increased or decreased to produce the desired wavelength. The processor 50 also may determine the amount of temperature adjustment that should be employed to produce the adjusted wavelength. The processor 50 may then set (block 126) the target temperature. For example, the processor 50 may store the target temperature within the ROM 56 or the nonvolatile storage 60.

The target temperature may then be used to measure the desired physiological parameter. For example, the method 100 (FIG. 7) may be performed to adjust the temperature control element 38 so that the light source 44 and/or 46 is at the target temperature for emitting the desired wavelength. Once the light source 44 and/or 46 is at the target temperature, the light source 44 and/or 46 may be used to emit light at the desired wavelength and determine the desired physiological characteristics. According to certain embodiments, the method 119 may be repeated to produce several different wavelengths using the light sources 44 and 46. For example, in certain embodiments, the temperature of the light sources 44 and 46 may be adjusted to so that the light sources emit various wavelengths corresponding to reduced hemoglobin, oxyhemoglobin, carboxyhemoglobin, and methemeglobin, which can then be subsequently used to determine total hemoglobin.

Figure 10:
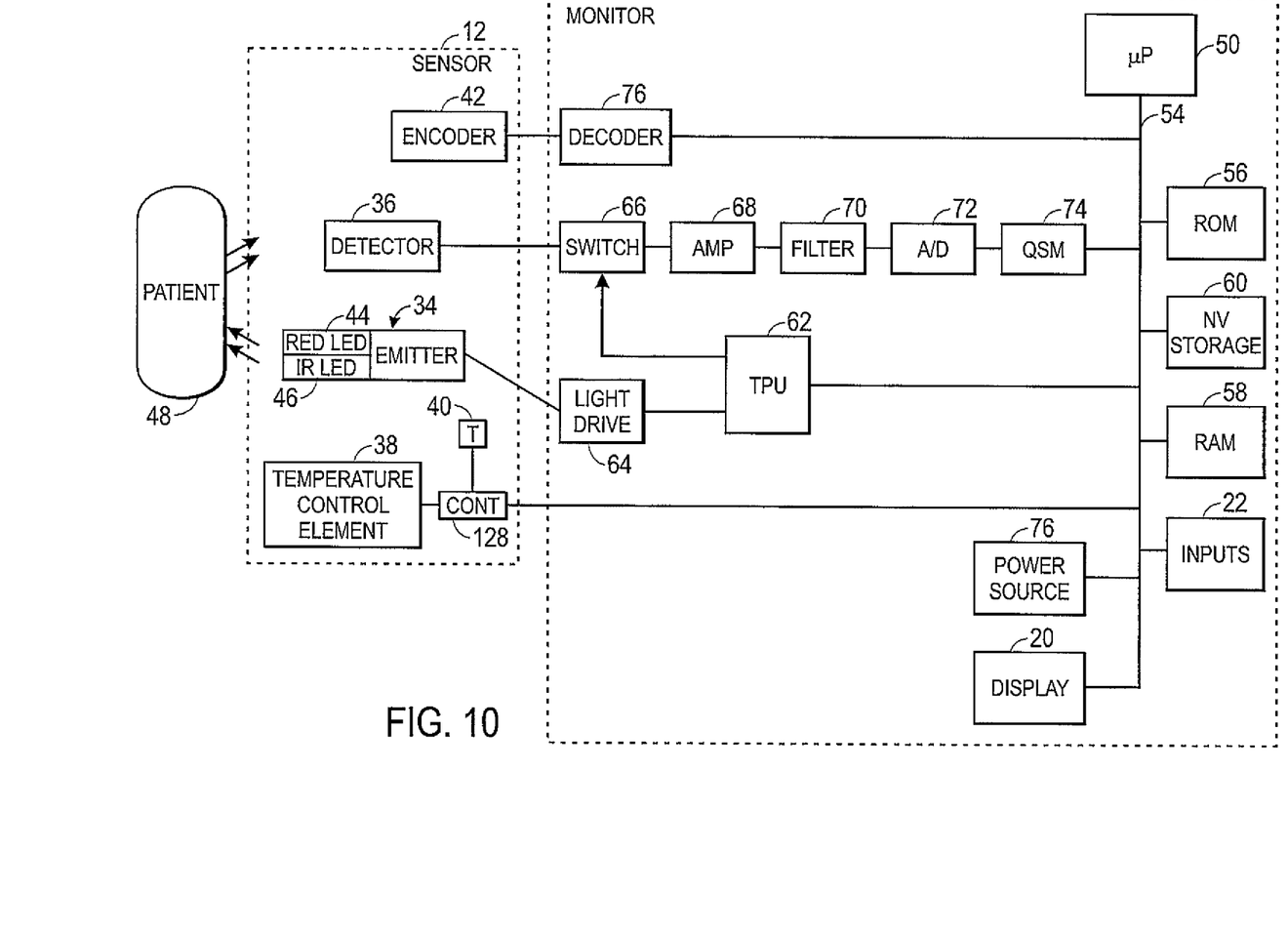
FIG. 10 is a block diagram of another embodiment of a sensor that can be coupled to the monitor of FIG. 1, in accordance with certain embodiments.

FIG. 10 depicts another embodiment of a medical monitor and sensor system that can be employed to control the temperature of light sources used to determine physiological parameters. The sensor and monitor system of FIG. 10 is generally similar to the system shown in FIG. 2. However, the sensor of FIG. 10 includes a separate controller 128 that can be employed to govern operation of the temperature control element 38. According to certain embodiments, the controller 128 may be thermostatic controller, a proportional controller, an analog or digital proportional, integral, and derivative (PID) controller, or a reduced instruction set controller (RISC), among others. The controller 128 may perform the method 100 as discussed above with respect to FIG. 7. Further, in certain embodiments, the controller 128 may determine the target temperature by performing the methods 110 and 119 described above with respect to FIGS. 8 and 9, respectively. However, in other embodiments, the processor 50 may be employed to determine the target temperature, which may then be provided to the controller 128.

Moreover, in other embodiments, the controller 128 may be replaced by a processor that governs one or more operations of the sensor 12. In these embodiments, the processor may be used to heat the emitter 34 in order to vary the wavelengths of the light sources. For example, the clock speed may be increased or a voltage regulator setting may be adjusted to provide heat for the emitter 34. The processor may operate in conjunction with the temperature control element 38 to provide heating for the emitter 34. For example, in certain embodiments, the temperature control element 38, may be designed to provide only cooling, while the processor provides heating. In another example, the processor may be designed to supplement the heating provided by the temperature control element 38. Further, in certain embodiments, the temperature control element 38 may be omitted and the processor may provide the sole source of heating for the emitter 34.

While the disclosure may be susceptible to various modifications and alternative forms, specific embodiments have been shown by way of example in the drawings and have been described in detail herein, However, it should be understood that the embodiments provided herein are not intended to be limited to the particular forms disclosed. Indeed, the disclosed embodiments may not only be applied to measurements of blood oxygen saturation, but these techniques may also be utilized for the measurement and/or analysis of other blood constituents. For example, the present techniques may be utilized for the measurement and/or analysis of earboxyhemoglobin, methemoglobin, total hemoglobin, fractional hemoglobin, intravascular dyes, and/or water content. Further, the various embodiments may cover all modifications, equivalents, and alternatives falling within the spirit and scope of the disclosure as defined by the following appended claims.

What is claimed is:

1. A system comprising:
   a sensor comprising:
      one or more light sources configured to emit one or more wavelengths of light corresponding to physiological parameters of a patient;
      an encoder storing data indicative of one or more peak wavelengths of light emitted by the one or more light sources;
      a thermoelectric element configured to provide cooling or heating to the one or more light sources to regulate the wavelengths of light emitted by the one or more light sources; and
   a monitor comprising:
      a decoder configured to receive the data indicative of the one or more peak wavelengths of light emitted by the one or more light sources;
      a processor configured to compare the one or more peak wavelengths to a calibration wavelength of a calibration profile included within the monitor to determine a target temperature for the one or more light sources that enables the one or more light sources to emit at least one of the wavelengths of light that correspond to the calibration wavelength; and
      a controller configured to adjust an amount of cooling or heating provided by the thermoelectric element to maintain the one or more light sources at the target temperature.

2. The system of claim 1, wherein the target temperature enables the one or more light sources to emit wavelengths of light corresponding to an isosbestic point.

3. The system of claim 1, further comprising a temperature sensor configured to detect a temperature of the one or more light sources, wherein the controller is configured to switch the thermoelectric element between a heating mode and a cooling mode based on the detected temperature.

4. The system of claim 3, wherein the controller is disposed within the sensor.

5. The system of claim 1, wherein the processor is configured to receive a signal generated based on the emitted wavelengths and to calculate the physiological parameters.

6. The system of claim 1, wherein the target temperature comprises a temperature range.

7. A method comprising:
   receiving data indicative of a peak wavelength of light emitted by one or more light sources at a monitor;
   determining, using a processor of the monitor, a target temperature for aligning the peak wavelength of light emitted by the one or more light sources with a calibration wavelength corresponding to a calibration profile of the monitor;
   detecting a temperature of the one or more light sources and comparing the detected temperature of the one or more light sources to the target temperature to determine a temperature adjustment; and
   adjusting operation of a temperature control element that provides cooling or heating to the one or more light sources based on the temperature adjustment to achieve the target temperature.

8. The method of claim 7, wherein adjusting operation of the temperature control element comprises adjusting a level of power provided to the temperature control element.

9. The method of claim 7, wherein adjusting operation of the temperature control element comprises switching a direction of current flowing through a thermoelectric element.

10. The method of claim 7, wherein determining the target temperature comprises comparing the peak wavelength of the one or more light sources to the calibration wavelength.

11. The method of claim 7, comprising emitting light at the calibration wavelength using the one or more light sources, receiving a signal generated based on the emitted light at the monitor, and calculating one or more physiological parameters based on the signal using the monitor.

12. The system of claim 1, wherein the thermoelectric element comprises a thermoelectric cooler.

13. The system of claim 1, wherein the thermoelectric element comprises a resistive heater.

14. The system of claim 1, wherein the thermoelectric element is switchable between a cooling mode and a heating mode.

15. A method comprising:
   receiving data indicative of a peak wavelength of light emitted by one or more light sources at a monitor;
   determining, using a processor of the monitor, a target temperature for aligning the peak wavelength of light emitted by the one or more light sources with a calibration wavelength corresponding to a calibration profile of the monitor, wherein determining the target temperature comprises comparing the peak wavelength of the one or more light sources to the calibration wavelength; and
   adjusting operation of a temperature control element that provides cooling or heating to the one or more light sources to achieve the target temperature.

16. The method of claim 15, wherein adjusting operation of the temperature control element comprises adjusting a level of power provided to the temperature control element.

17. The method of claim 15, wherein adjusting operation of the temperature control element comprises switching a direction of current flowing through a thermoelectric element.

18. The method of claim 15, comprising emitting light at the calibration wavelength using the one or more light sources, receiving a signal generated based on the emitted light at the monitor, and calculating one or more physiological parameters based on the signal using the monitor.

19. A system comprising:
   a sensor comprising:
      one or more light sources configured to emit one or more wavelengths of light corresponding to physiological parameters of a patient;
      an encoder storing data indicative of one or more peak wavelengths of light emitted by the one or more light sources;
      a thermoelectric element configured to provide cooling or heating to the one or more light sources to regulate the wavelengths of light emitted by the one or more light sources;
   a monitor comprising:
      a decoder configured to receive the data indicative of the one or more peak wavelengths of light emitted by the one or more light sources;
      a processor configured to determine a target temperature for aligning the one or more peak wavelengths of light emitted by the one or more light sources with a calibration wavelength corresponding to a calibration profile of the monitor, to detect a temperature of the one or more light sources, and to compare the detected temperature of the one or more light sources to the target temperature to determine a temperature adjustment; and a controller configured to adjust an amount of cooling or heating provided by the thermoelectric element based on the temperature adjustment to maintain the one or more light sources at the target temperature.

20. The system of claim 19, wherein the processor is configured to compare the one or more peak wavelengths to the calibration wavelength of the calibration profile included within the monitor to determine the target temperature.

* * * * *